United States Patent [19]
Sasaki et al.

[11] Patent Number: 5,469,849
[45] Date of Patent: Nov. 28, 1995

[54] ULTRASOUND DIAGNOSIS APPARATUS

[75] Inventors: Hiroshi Sasaki; Hiroyuki Tsujino, both of Tochigi, Japan

[73] Assignee: Kabushiki Kaisha Toshiba, Kawasaki, Japan

[21] Appl. No.: 260,364

[22] Filed: Jun. 14, 1994

[30] Foreign Application Priority Data

Jun. 14, 1993 [JP] Japan .................................. 5-141863

[51] Int. Cl.⁶ .................................................. A61B 8/00
[52] U.S. Cl. ............................ 128/660.07; 128/662.02
[58] Field of Search ........................ 128/660.01, 660.07, 128/661.01, 661.03, 661.04, 660.04, 660.05, 662.06

[56]  References Cited

U.S. PATENT DOCUMENTS

5,040,537  8/1991  Katakura ..................... 128/662.02 X
5,135,000  8/1992  Akselrod et al. ................... 128/662.02
5,345,938  9/1994  Nishiki et al. ...................... 128/660.04

*Primary Examiner*—Francis Jaworski
*Attorney, Agent, or Firm*—Oblon, Spivak, McClelland, Maier & Neustadt

[57] ABSTRACT

An ultrasound diagnosis apparatus for obtaining an ultrasound image used with a contrast agent is disclosed. Various kinds of data relating the contrast agent can be inputted or selected and they can also be displayed with the ultrasound image on a same display. The data inputted or selected can be used for controlling condition of the system. Further, information of time related to the examination using the contrast agent can be displayed on the display.

26 Claims, 6 Drawing Sheets

ULTRASOUND DIAGNOSIS APPARATUS

BACKGROUND OF THE INVENTION

This invention relates to an ultrasound diagnosis apparatus. More specifically, this invention relates to an ultrasound diagnosis apparatus for obtaining an ultrasound image of a patient using an ultrasound contrast agent.

An ultrasound diagnosis apparatus, which obtains a tomographic image of soft tissues of a living body using echo signals, is one of the most popular applications of ultrasound technique in medical use. This technique has great advantages because of its non-invasiveness, non X-ray dosing or real-time imaging, etc., comparing to other diagnosis apparatuses such as an X-ray apparatus, an X-ray CT, a magnetic resonance imaging apparatus or a nuclear medicine apparatus. Therefore, it is broadly used in circulation system, urological or gynecological departments in a hospital. Especially, it is greatly useful in displaying motion of a heart or a fetus.

Recently, a new examination method of blood movement using a contrast agent injected from a vein has been offered. Because of less-invasiveness, it is becoming popular. The examination includes monitoring variations of a distribution of the contrast agent, or obtaining a delay time of the contrast agent from injection to reaching a region of interest (ROI) and a time-density curve (TDC) representing a variation of brightness in the ROI. Information of the contrast agent used, such as a name, density (mg/ml), injected volume (ml), injection speed (ml/sec) and injection position of the patient is significant and filled in a specific form by an operator.

However, it is inconvenient to fill the information in the form by hand-writing. Further, although it is possible to input the information from a keyboard and display on a screen in a conventional ultrasonic diagnosis apparatus, it may take a long time to input and is also inconvenient.

SUMMARY OF THE INVENTION

Accordingly, it is an object of the present invention to provide an improved ultrasound diagnosis apparatus for obtaining an ultrasound image with a contrast agent.

It is a further object of the present invention to provide an improved ultrasound diagnosis apparatus in displaying information of a contrast agent.

In accordance with the present invention, the foregoing objects, among others, are achieved by providing an ultrasound diagnosis apparatus for obtaining ultrasound images of a patient, comprising transmission-reception means for transmitting ultrasound signals and receiving echo signals, image processing means for processing an ultrasound image according to the echo signals, setting means for setting data related to a contrast agent, first memory means for storing data the data being set by the setting means, and display means for displaying the ultrasound image and the data on a screen.

In accordance with another aspect of the present invention, the above-stated objects are achieved by providing an ultrasound diagnosis apparatus for obtaining an ultrasound image of a patient, comprising transmission-reception means for transmitting ultrasound signals and receiving echo signals, image processing means for processing an ultrasound image according to the echo signals, counter means for counting time, counter control means for controlling a counting period of the counter means, and display means for displaying the ultrasound image and the time counted by the counter means on a screen.

There has also been provided, in accordance with yet another aspect of the present invention, an ultrasound diagnosis apparatus for obtaining ultrasound images of a patient, comprising transmission-reception means for transmitting ultrasound signals and receiving echo signals, image processing means for processing an ultrasound image according to the echo signals, setting means for setting data related to a contrast agent, first memory means for storing data the data being set by the setting means, display means for displaying the ultrasound image and the data on a screen, and condition control means for controlling contrast of the ultrasound image to be displayed on the display means according to the data being set by the data setting means.

BRIEF DESCRIPTION OF THE DRAWINGS

For a more complete understanding of the present invention, reference will be made to the following detailed explanations in conjunction with the accompanying drawings in which.

DESCRIPTION OF PREFERRED EMBODIMENTS

Referring now to figures, embodiments of the present invention will be described below.

Basic Structure

Figure 1:
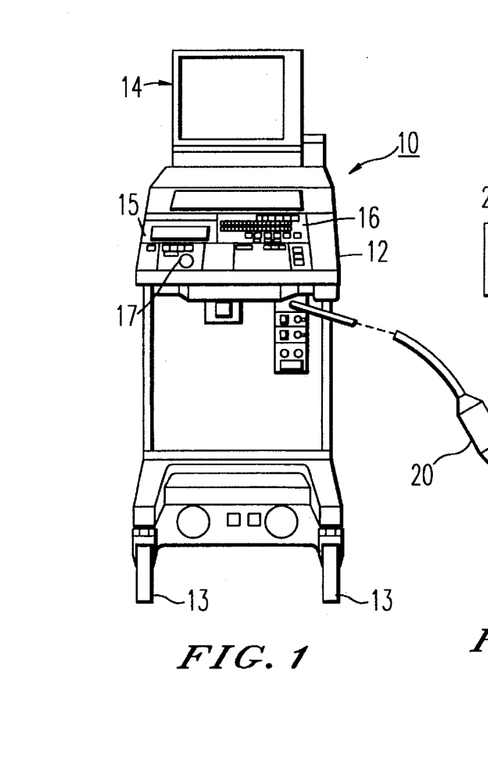
FIG. 1 shows a perspective view of an ultrasound diagnosis apparatus.

FIG. 1 shows a whole view of an ultrasound diagnosis apparatus 10. The ultrasound diagnosis apparatus 10 comprises a main unit 12, casters 13 and a display unit 14. The main unit 12 includes a computer for processing an ultrasound image, and an operation panel 15 which includes a keyboard 16, a trackball 17 and other buttons to be operated by an operator. The display unit 14, such as a CRT, for displaying an ultrasound image is mounted on the main unit 12. Further, a sector type probe 20 is detachably connected to the main unit 12. Various types of probes, other than the sector type, such as convex, linear, oblique or mechanical, can be connected to the main unit 12.

Figure 2:
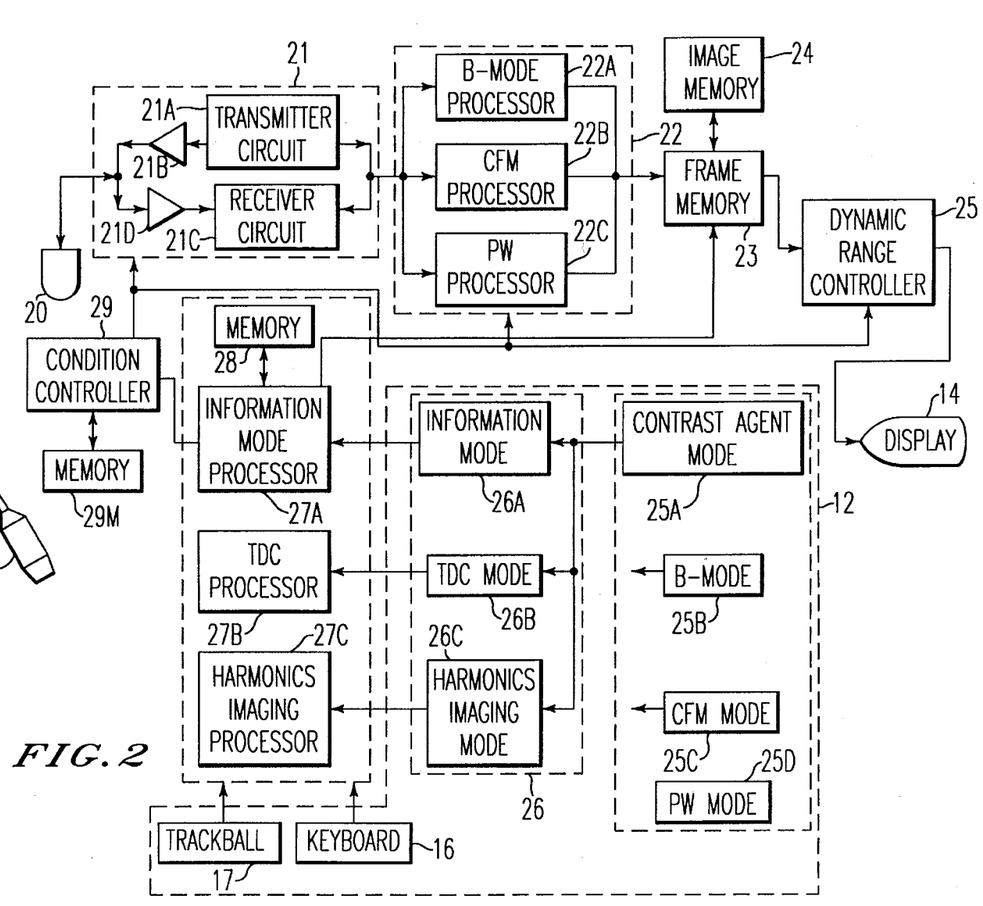
FIG. 2 shows a block diagram of a first embodiment.

FIG. 2 shows a block diagram of the ultrasound diagnosis apparatus of a first embodiment. The sector-type probe 20, comprising an array of a plurality of transducers, transmits ultrasound waves into an object. A transmitter/receiver (T/R) unit 21 is connected to the probe 20. A transmitter circuit 21A in the T/R unit 21 supplies driving pulses through a transmitter amplifier 21B to each of the transducers in the probe 20 and controls delay times of the driving pulses such that an ultrasound beam is transmitted in a desired direction.

The transmitted ultrasound waves reflect in the object and the reflected echoes are received by the probe 20. The received echo signals are inputted to the T/R unit 21. A receiver circuit 21C controls delay times of the received signals inputted through a receiver preamplifier 21D. The received signals are processed in one of a B-mode processor 22A, a Color Flow Mapping (CFM) processor 22B and a Pulse Wave (PW) processor 22C to produce an ultrasound image according to the selected mode and the produced image is stored in a frame memory 23. The produced ultrasound image is read out from the frame memory 23 through a dynamic range controller 25 and displayed on a screen of the display unit 14. An image memory 24 stores plural frames of the images. Dynamic range of the signals can also be controlled in the T/R unit 21, the image processor 22 and the frame memory 23.

Mode selection buttons 25A–D are provided on the operation panel 15. The buttons 25A–D include, for example, a Contrast Agent Mode button 25A, a B-Mode button 25B, a CFM Mode button 25C and a PW Mode button 25D. The operator can select one of the modes by pushing one of the buttons 25A–D. When the operator selects one of the buttons 25A–C, one of the processors 22A–C starts and a conventional ultrasound imaging is carried out. When the operator is going to obtain an ultrasound image using a contrast agent, the Contrast Agent Mode 25D should be selected. After pushing the Contrast Agent Mode button 25D, the operator can select sub-modes by pushing one of sub-mode selection buttons 26A–C also provided on the operation panel 15. The sub-mode selection buttons 26A–C include an Information Mode button 26A, a TDC Mode button 26B and a Harmonics Imaging Mode button 26C. When the Information Mode button 26A in pushed, an Information Mode processor 27A works to start an Information Mode. In the Input Mode, a condition controller 29 controls the T/R unit 21, the processors 22A–C and a dynamic range controller 25 according to an output of the Information Mode processor 27A. Operations of the Information Mode will be described later in detail. When the TDC Mode button 26B is pushed, an TDC processor 27B works to start a TDC Mode. Pushing the Harmonics Imaging Mode button 26C, a Harmonics Imaging processor 27C works to start a Harmonics Imaging Mode. The TDC mode and the Harmonics Imaging Mode are conventional and the present invention is not limited to these sub-modes. The information data related the contrast agent to be set during the Information Mode is stored in a memory 28.

Information Mode

Referring now to FIGS. 2–5, operations of the Information Mode for setting (inputting or selecting) information regarding contrast agent will be described.

Figure 3A:
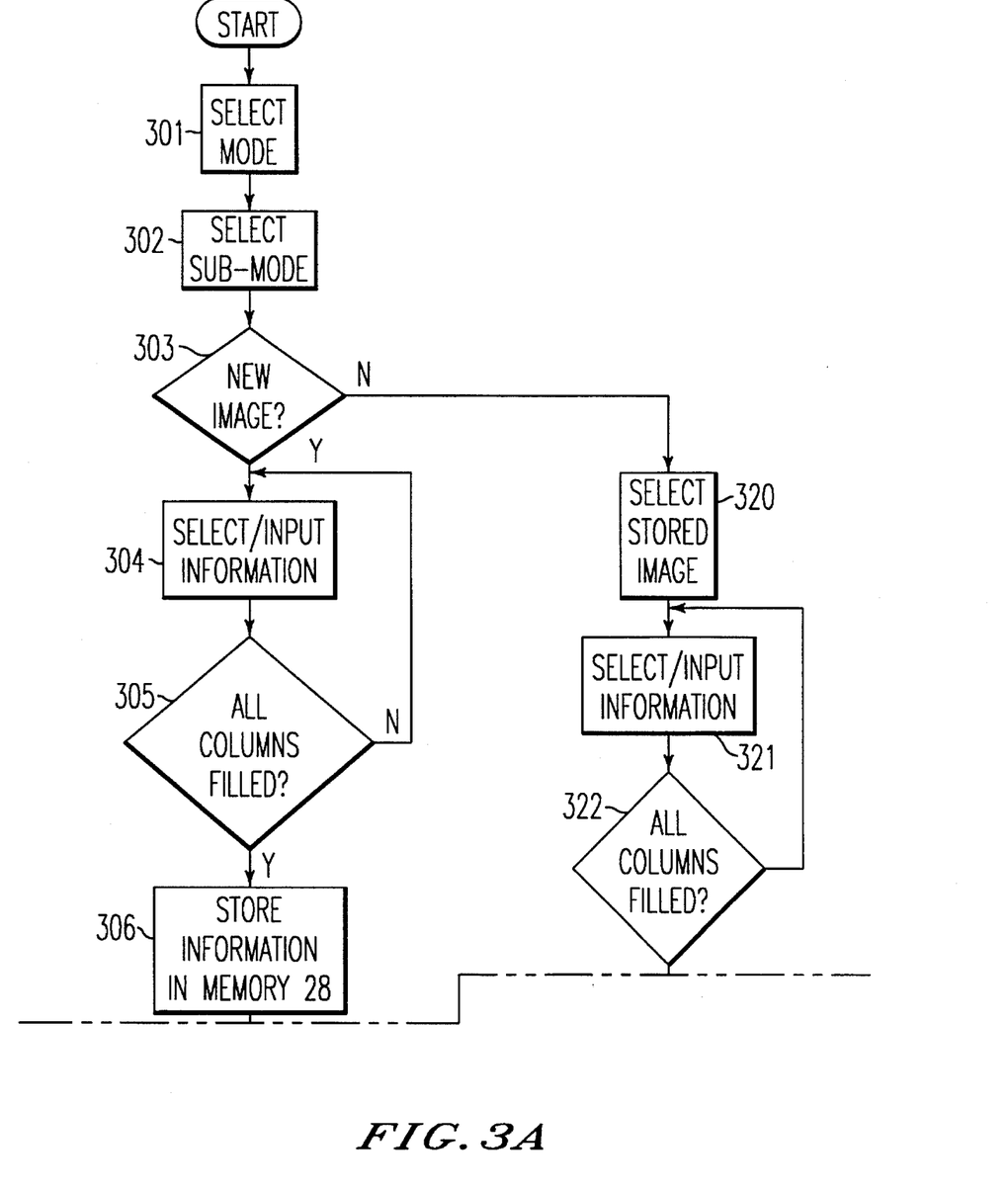
FIG. 3 shows a flow chart of an operation of the first embodiment.
Figure 3B:
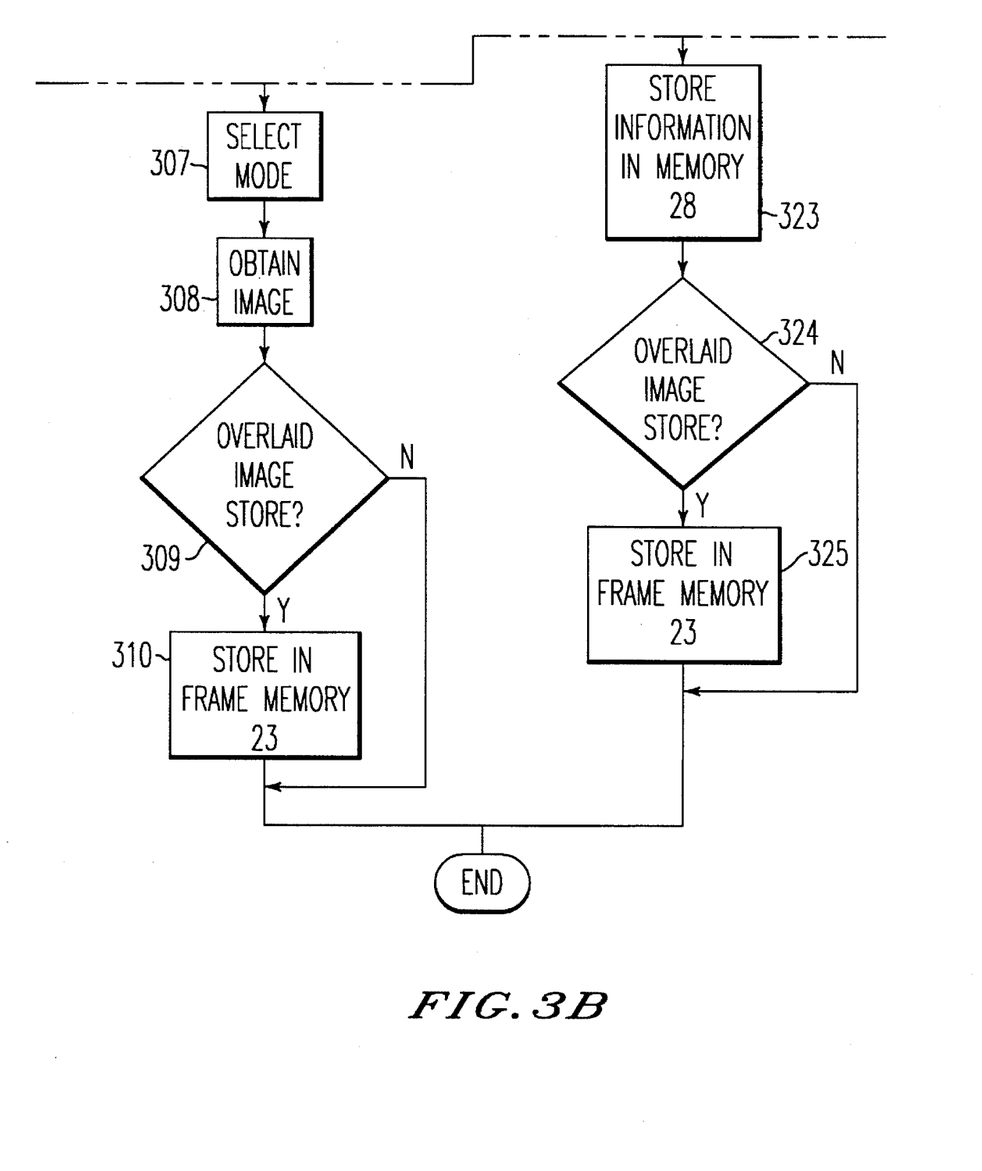
Figure 4:
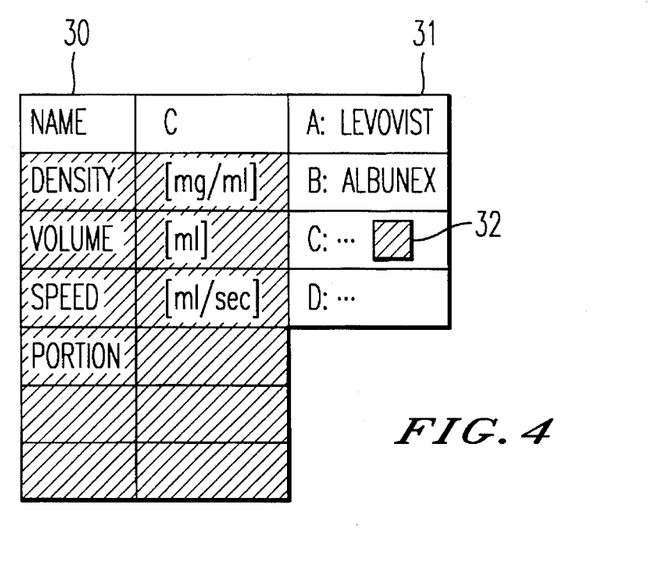
FIG. 4 shows a display example of a table.
Figure 5:
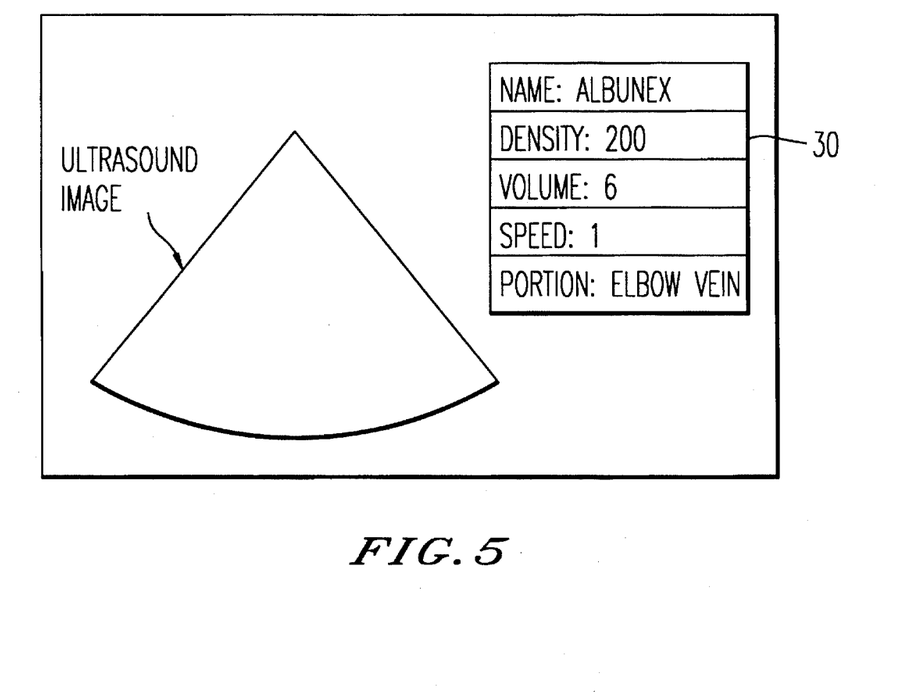
FIG. 5 shows a display example of an ultrasound image with a contrast agent information overlaid thereon.

First, the Contrast Agent Mode starts by pushing the Contrast Agent Mode Button 25A (Step 301 in FIG. 3). The Information Mode starts by pushing the Information Mode button 26A (Step 302). The Information Mode can be used to input information of a contrast agent appearing in images which the operator is going to obtain or which are already stored in the image memory 24. When the Information Mode starts, the display 14 displays an instruction to select the next procedure, e.g., "obtaining new images" or "reading out stored images" (Step 303). The former procedure will be described first. After selecting "obtaining new images", a main table 30 shown in FIG. 4 is read out from the memory 28 and displayed on the display 14. The main table 30 includes columns to be filled with data regarding the contrast agent, such as "Name", "Density", "Volume", "Injection Speed", and "Injection Position". A sub-table 31 including a plurality of columns is also displayed in connection with one of the columns in the main columns 30. In FIG. 4, a plurality of names of contrast agents, often used in ultrasound examinations, which are stored in the memory 28 are shown in the sub-column 31 in connection with the column of "Name". Then the operator selects one of the displayed names by operating the trackball 17 to move a cursor 32 (Step 304). After selecting one of the names, the next set of data related to densities of the selected contrast agent will be displayed in the next sub-column. Various sets of data related to other columns are also stored in the memory 28 and displayed to be selected in turn. Similar steps are repeated until all the columns are filled (Step 305).

In the above-described embodiment, the number of columns to be filled is five, however, this invention is not limited thereto. The items in the memory 28 to be displayed in the sub-columns may be deleted or added by the operator. Further, operations such as filling the columns or selecting sub-modes may be operated manually from the keyboard 16.

After filling all the columns with data by the operator in the above-mentioned manner, the selected or inputted data are stored in the memory 28, the Information Mode finishes (Step 306) and an ultrasound imaging will be ready. The displayed table 30 may be copied by a printer or a camera. Then the operator selects one of the mode selection buttons 25B–D (Step 307) and obtains ultrasound images using the contrast agent in the selected imaging mode (Step 308). Each frame of the obtained image is stored in the frame memory 23 and expanded into a two-dimensional matrix. In the frame memory 23, the table 30 filled in the Information Mode is overlaid on each frame at an address corresponding to a predetermined position on the screen of the display 14. The predetermined position on which the table 30 is overlaid is preferred not to overlap with the ultrasound image. The overlaid images are read out from the frame memory 23 in a predetermined order to be displayed on the display 14. For finishing the Contrast Agent Mode, the operator selects whether to store the overlaid images in the image memory 24 according to an instruction displayed on the display 14 (Step 309). When storing, the images with the overlaid table 30 are read out from the frame memory 23 and stored in the image memory 24 (Step 310). According to this embodiment, the images stored in the image memory can be displayed always with information of the contrast agent.

Otherwise, information of the contrast agent can be added to images which have already been obtained when the operator selects "reading out stored images" at Step 303. The operator selects an image stored in the image memory 24 to be read out through the frame memory 23 (Step 320). In the frame memory 23, the table 30 with blank columns is overlaid at a predetermined address and the overlaid image is displayed on the display 14. Then the operator selects or inputs information of the contrast agent in a similar manner as described above (Steps 321–323). After finishing inputting information, the table 30 filled with data of the contrast agent can be added to each frame of the stored images at a predetermined address in the image memory 24 (Steps 324, 325).

The above-described sequence of the Information Mode is programmed in the Information Mode Processor 27A. The present invention is not limited to the above-described sequence and many alternatives may be possible.

Condition Control

According to the first embodiment, information being set can be used for controlling condition of the system, for example, contrast of the image.

In an ultrasound imaging using a contrast agent, brightness of pixels corresponding to the contrast agent on a display greatly increases because of high intensity of backscattered signals. However, in a conventional ultrasound diagnosis apparatus, the dynamic range of the brightness being set in a range of signal intensity which is expected in echo signals reflected in an ordinary living body. Therefore, a component of the contrast agent in the echo signals may exceed the dynamic range of the system and cause a saturated image which interferes observing the image. To prevent such a disadvantage, the brightness of the image can be controlled according to information being set in the Information Mode.

The increase in a signal intensity is determined by parameters related to injected contrast agent, such as type, density and volume. For example, when the amount of the injected contrast agent is 200 mg/ml, the increase in the signal intensity is approximately 10 dB. A memory 29M connected to the condition controller 29 stores a look-up table for referring to relationships between the parameters regarding the contrast agent and the increase in the signal intensity. When the operator obtains ultrasound images, according to the data stored in the memory 28 during the Information Mode, data of the increase corresponding to the selected contrast agent is inputted into the condition controller 29. Then the condition controller 29 controls a gain of the preamplifier 21D according to the data of the increase. For a sufficient control, a power of the transmitter amplifier 21B may also be controlled. In addition, contrast can be controlled in the processors 22A–C. Further, when the operator adds contrast agent information to the images already obtained, the condition controller 29 controls the dynamic range controller 25 according to the inputted data from the Information Mode processor 27A to display ultrasound images with optimum contrast.

The scope of the present invention is not limited to the above-described second embodiment. For example, the dynamic range controller 25 may be controlled during obtaining images. Further, a fine control of the gain of the receiver amplifier 21D or the power of the transmitter amplifier 21A may be performed manually by the operator. Furthermore, a sensitivity-time controller (STC) may be controlled by the condition controller 29.

Time Display

Figure 7:
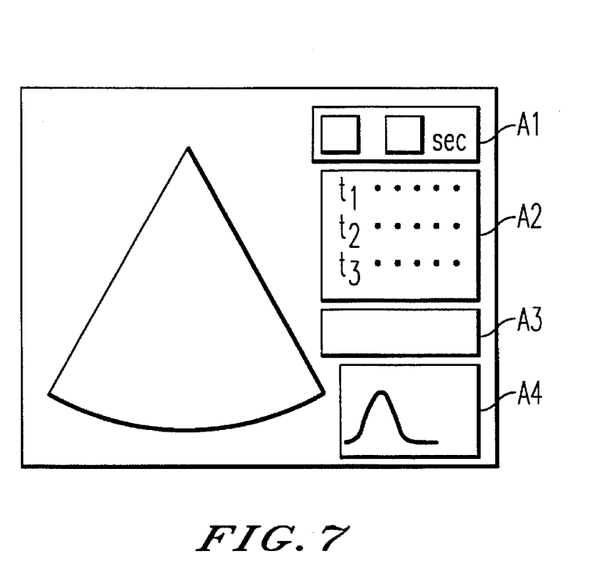
FIG. 7 shows a display example of an ultrasound image with a time information overlaid thereon.
Figure 8:
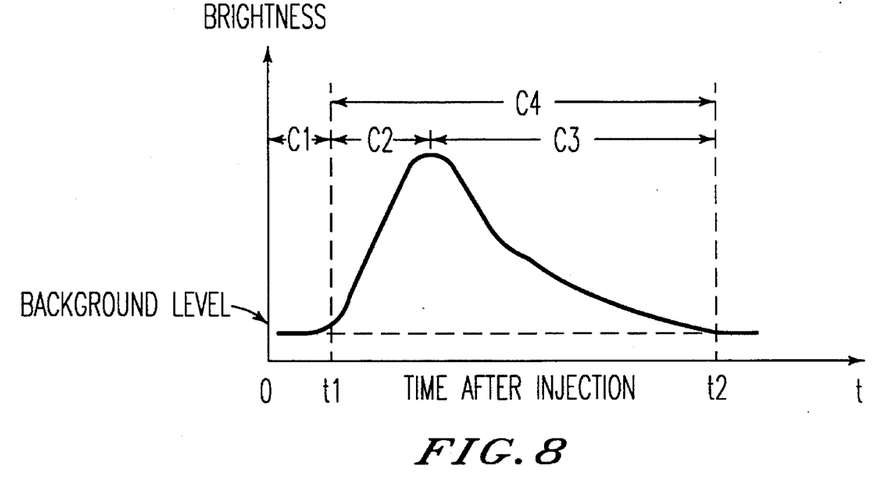
FIG. 8 is an example of a time-density curve.

Next, a second embodiment of the present invention will be described referring to FIGS. 6–8.

In an ultrasound examination using a contrast agent, various kinds of data related to time are obtained. For example, a variation of a spatial distribution of the contrast agent or a Time Density Curve (TDC) may be obtained. To obtain these data, it is required for the operator to count time from a starting time, e.g., starting or finishing injection of the contrast agent. In the second embodiment, time from injection of the contrast agent is counted and displayed.

Figure 6:
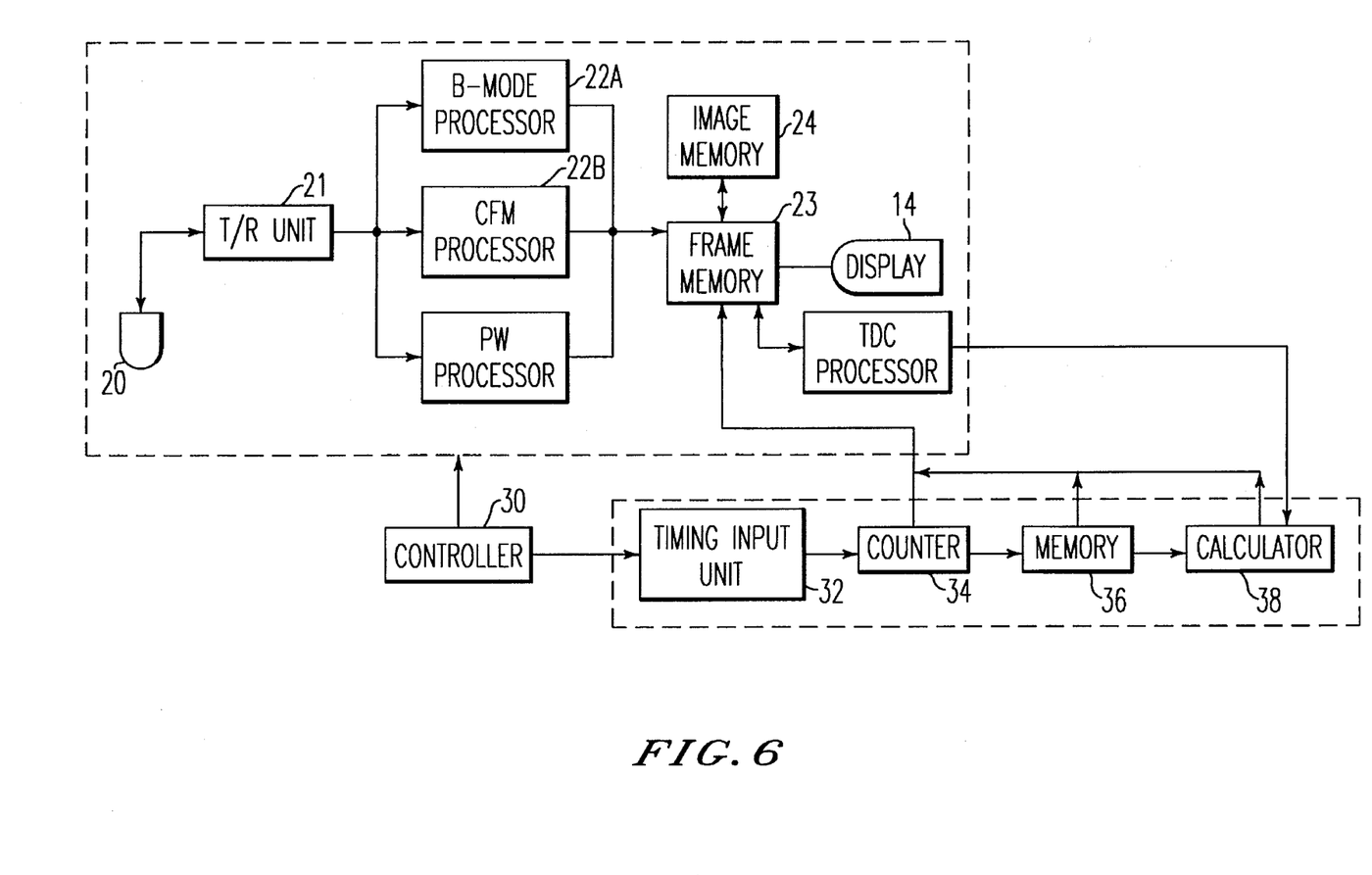
FIG. 6 shows a block diagram of a second embodiment.

FIG. 6 is a block diagram of the second embodiment.

A timing input unit 32 including a start button and a stop button is provided on the operation panel 15. A counter 34 counts time and a starting time, lap times and a finishing time are inputted into the frame memory 23 and a memory 36. A calculator 38 calculates various characterizing periods according to the counted times. A TDC processor 40 produces a TDC of a ROI according to plural frames of ultrasound images stored in the frame memory 23 and the TDC is overlaid on the images in the frame memory 23 to be displayed on the display 14.

To start counting time, the operator starts a Time mode. The Time mode may be included in the sub-modes described in the first embodiment. In the Time mode, a present time area A1 for displaying a time passed from the starting time, a lap time area A2 for displaying several lap times and a characterizing period area A3 for displaying several characterizing periods calculated in the calculator 38 are provided at the predetermined locations on the display 14 as shown in FIG. 7. Before injection, the present time area A1 shows "0.0 sec". This may blink for enhancing. A TDC area A4 for displaying a TDC is also provided at the predetermined location on the display 14. The operator can designate a ROI at a point where the contrast agent is expected to appear using the trackball 17. When the operator pushes the start button simultaneously with injection of the contrast agent, the counter 34 starts counting and the time from the starting time is displayed in the present time area A1. Characters displayed in the present time area A1 is preferably larger than those in the other areas A2 and A3 for an easy observation. This is advantageous in a video replay in which an image quality may be degraded. A TDC is produced and displayed in the TDC area.

Operations of the second embodiment of the present invention will be described below.

First, the operator starts the Time mode and sets a ROI on the display 14 at a point where the contrast agent is expected to appear. Then the operator injects the contrast agent and at the same time the operator pushes the start button to start counting time and display a TDC. FIG. 8 shows a TDC to be displayed in the TDC area A4 of the display 14. At a time t1, the contrast agent reaches the organ of the object corresponding to the ROI and the brightness of pixels in the ROI begins to increase. The operator pushes the start button and a lap time t1 is stored in the memory 36 and displayed in the lap time area A2. Counting in the counter 34 continues after displaying the first lap time t1. Then at a time t2 when the contrast agent passes the ROI and the brightness reaches the background level, the operator pushes the stop button to stop the counter 34 and a lap time t2 is also stored in the memory 36 and displayed below the lap time t1 in the lap time area A2. According to the obtained lap times t1 and t2, the calculator calculates a plurality of characterizing periods, e.g., a period from the start time to the time the contrast agent reaches the ROI C1, a period to the time the brightness reaches a peak level C2, a period from the peak to the background level C3 and a period of the contrast agent effect duration C4. The period C4 is obtained by calculation (t2–t1). The obtained characterizing periods C1–C4 are displayed in the characterizing period area A4. The present invention is not limited to the above-described sequence of calculation and many alternatives may be possible.

The present invention is not limited to the above-described second embodiment. For example, inputting the start time, the lap times t1 and t2 may be performed automatically. For the automatic input, an injector for injecting the contrast agent may be electrically connected to the timing input unit 32 to detect the beginning or finishing injection. Otherwise, these timings may be inputted from a foot switch electrically connected to the timing input unit 32. Further, the lap times t1 and t2 may also be determined automatically. For example, a time when the TDC goes above a predetermined threshold level is assigned as t1 and a time when the TDC goes below the threshold is t2. Further, the peak level of the brightness may be determined by detecting a time when a differential value of the TDC is zero.

Although the present invention has been described with reference to preferred embodiments, numerous modifications and rearrangements can be made, and still come within the scope of the invention.

What is claimed is:

1. An ultrasound diagnosis apparatus for obtaining ultrasound images of a patient, comprising;

transmission-reception means for transmitting ultrasound signals and receiving echo signals;

image processing means for processing an ultrasound image according to the echo signals;

setting means for setting data related to a contrast agent;

first memory means for storing data the data being set by the setting means; and display means for displaying the ultrasound image and the data on a screen.

2. The ultrasound diagnosis apparatus according to claim 1, the first memory means storing plural sets of data, the data setting means selecting one of the sets of data and the display means displaying the ultrasound image and the selected set of data.

3. The ultrasound diagnosis apparatus according to claim 1, the data setting means including an operation panel for inputting the data.

4. The ultrasound diagnosis apparatus according to claim 3, the operation panel including a keyboard.

5. The ultrasound diagnosis apparatus according to claim 3, the operation panel including a trackball.

6. The ultrasound diagnosis apparatus according to claim 1, further comprising:

condition control means for controlling at least one of the transmission-reception means, the image processing means and the display means according to the data being set by the data setting means.

7. The ultrasound diagnosis apparatus according to claim 6, further comprising:

second memory means for storing a relationship between the data and the condition.

8. The ultrasound diagnosis apparatus according to claim 6, the transmission-reception means including a transmitter amplifier and a receiver amplifier, wherein the condition control means controls at least one of gain of the receiver amplifier and power of the transmitter amplifier.

9. The ultrasound diagnosis apparatus according to claim 6, the condition control means controlling the image processing means.

10. The ultrasound diagnosis apparatus according to claim 6, the condition control means controlling contrast of the display means.

11. The ultrasound diagnosis apparatus according to claim 1, further comprising overlay means for overlaying the data on the ultrasound image.

12. The ultrasound diagnosis apparatus according to claim 11, further comprising a third memory means for storing the ultrasound image with the overlaid data.

13. The ultrasound diagnosis apparatus according to claim 1, wherein the data is at least one of a name, density, volume, injection speed and injection position of the contrast agent.

14. An ultrasound diagnosis apparatus for obtaining an ultrasound image of a patient, comprising;

transmission-reception means for transmitting ultrasound signals and receiving echo signals;

image processing means for processing an ultrasound image according to the echo signals;

counter means for counting time;

counter control means for controlling a counting period of the counter means;

display means for displaying the ultrasound image and the time counted by the counter means on a screen; and timing input means for inputting a timing for at least one of starting the counter means, obtaining a lap time and stopping the counter means.

15. The ultrasound diagnosis apparatus according to claim 14, further comprising a time-density curve forming means for forming a time-density curve representing a density variation of a contrast agent in the ultrasound image formed by the image forming means.

16. The ultrasound diagnosis apparatus according to claim 15, wherein the time-density curve formed by the time-density curve forming means is displayed on the screen.

17. The ultrasound diagnosis apparatus according to claim 14, the timing input means comprising a button.

18. The ultrasound diagnosis apparatus according to claim 14, the timing input means being electrically connected to an injector for injecting a contrast agent into the patient.

19. The ultrasound diagnosis apparatus according to claim 14, the timing input means comprising a foot switch.

20. The ultrasound diagnosis apparatus according to claim 14, further comprising calculation means for calculating a predetermined characteristic period according to the timing.

21. An ultrasound diagnosis apparatus for obtaining ultrasound images of a patient, comprising;

transmission-reception means for transmitting ultrasound signals and receiving echo signals;

image processing means for processing an ultrasound image according to the echo signals;

setting means for setting data related to a contrast agent;

first memory means for storing data the data being set by the setting means;

display means for displaying the ultrasound image and the data on a screen; and condition control means for controlling at least one of the transmission-reception means, the image processing means and the display means according to the data being set by the data setting means.

22. The ultrasound diagnosis apparatus according to claim 21, further comprising:

second memory means for storing a relationship between the data and a condition for controlling the contrast.

23. The ultrasound diagnosis apparatus according to claim 21, the transmission-reception means including a transmitter amplifier and a receiver amplifier, wherein the condition control means controls at least one of gain of the receiver amplifier and power of the transmitter amplifier.

24. The ultrasound diagnosis apparatus according to claim 21, the condition control means controlling the image processing means.

25. The ultrasound diagnosis apparatus according to claim 21, the condition control means controlling contrast of the display means.

26. An ultrasound diagnosis apparatus for obtaining ultrasound images of a patient, comprising;
- means for transmitting ultrasound signals and receiving echo signals;
- means for processing an ultrasound image according to the echo signals;
- means for setting data related to a contrast agent;
- means for storing data the data being set by the setting means;
- means for displaying the ultrasound image and the data on a screen; and
- means for controlling contrast of the ultrasound images to be displayed according to the data.

* * * * *